(12) United States Patent
Angell et al.

(10) Patent No.: US 11,145,393 B2
(45) Date of Patent: Oct. 12, 2021

(54) CONTROLLING EQUIPMENT IN A PATIENT CARE FACILITY BASED ON NEVER-EVENT COHORTS FROM PATIENT CARE DATA

(71) Applicant: International Business Machines Corporation, Armonk, NY (US)

(72) Inventors: Robert L. Angell, Salt Lake City, UT (US); Robert R. Friedlander, Southbury, CT (US); Richard Hennessy, Austin, TX (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 557 days.

(21) Appl. No.: 15/800,860

(22) Filed: Nov. 1, 2017

(65) Prior Publication Data
US 2018/0075193 A1 Mar. 15, 2018

Related U.S. Application Data

(63) Continuation-in-part of application No. 12/335,857, filed on Dec. 16, 2008, now abandoned.

(51) Int. Cl.
*G16H 10/60* (2018.01)
*G16H 10/20* (2018.01)
(Continued)

(52) U.S. Cl.
CPC .............. *G16H 10/60* (2018.01); *G16H 10/20* (2018.01); *G16H 50/70* (2018.01); *G16H 70/20* (2018.01)

(58) Field of Classification Search
CPC ........ G16H 10/60; G16H 50/70; G16H 70/20; G16H 10/20; G06Q 50/24; G06Q 50/22–24; G06F 19/324
See application file for complete search history.

(56) References Cited

U.S. PATENT DOCUMENTS 4,742,388 A 5/1988 Cooper et al.
5,036,462 A 7/1991 Kaufman et al.
(Continued)

FOREIGN PATENT DOCUMENTS

KR 20080082924 A 9/2008

OTHER PUBLICATIONS

U.S. Appl. No. 12/333,326—Non-Final Office Action dated May 16, 2012, pp. 1-12.
(Continued)

*Primary Examiner* — Robert A Sorey
(74) *Attorney, Agent, or Firm* — Law Office of Jim Boice

(57) ABSTRACT

A computer implemented method modifies a unit of medical equipment based on never-event cohorts, where a never-event is a preventable error experienced by a patient while receiving medical care. One or more processors process patient care data to form digital patient care data. The processor(s) analyze the digital patient care data using cohort criteria to identify a set of never-event attributes from the set of patient care patterns. The processor(s) receive, from a set of sensors, facility event data that describe an electrical fault in a unit of medical equipment used on patients in the patient care facility in order to modify the digital patient care data, and then modify the unit of medical equipment in order to correct the electrical fault based on the modified digital patient care data.

18 Claims, 6 Drawing Sheets

(51) Int. Cl.
*G16H 50/70* (2018.01)
*G16H 70/20* (2018.01)

(56) References Cited

U.S. PATENT DOCUMENTS

| | | | |
|---|---|---|---|
| 5,664,109 A | 9/1997 | Johnson et al. | |
| 5,774,569 A | 6/1998 | Waldenmaier | |
| 6,054,928 A | 4/2000 | Lemelson et al. | |
| 6,119,096 A | 9/2000 | Mann et al. | |
| 6,178,141 B1 | 1/2001 | Duckworth et al. | |
| 6,242,186 B1 | 6/2001 | Salonen | |
| 6,553,336 B1 | 4/2003 | Johnson et al. | |
| 6,646,676 B1 | 11/2003 | Dagraca et al. | |
| 6,795,808 B1 | 9/2004 | Strubbe et al. | |
| 7,308,385 B2 | 12/2007 | Wegerich et al. | |
| 7,363,309 B1 | 4/2008 | Waite et al. | |
| 7,492,943 B2 | 2/2009 | Li et al. | |
| 7,538,658 B2 | 5/2009 | Twitchell | |
| 7,548,874 B2 | 6/2009 | Kanevsky et al. | |
| 7,584,280 B2 | 9/2009 | Kim et al. | |
| 7,634,109 B2 | 12/2009 | Steinberg et al. | |
| 7,667,596 B2 | 2/2010 | Ozdemir et al. | |
| 7,683,929 B2 | 3/2010 | Elazar et al. | |
| 7,755,480 B2 | 7/2010 | Aritsuka et al. | |
| 7,840,515 B2 | 11/2010 | Ozdemir et al. | |
| 7,840,897 B2 | 11/2010 | Ancier | |
| 7,846,020 B2 | 12/2010 | Walker et al. | |
| 7,921,036 B1 | 4/2011 | Sharma et al. | |
| 7,930,204 B1 | 4/2011 | Sharma et al. | |
| 7,953,686 B2 | 5/2011 | Angell et al. | |
| 7,974,869 B1 | 7/2011 | Sharma et al. | |
| 8,000,777 B2 | 8/2011 | Jaeb et al. | |
| 8,041,516 B2 | 10/2011 | Angell et al. | |
| 8,117,144 B2 | 2/2012 | Angell et al. | |
| 8,321,797 B2 | 11/2012 | Perkins | |
| 2002/0176604 A1 | 11/2002 | Shekhar et al. | |
| 2002/0183971 A1 | 12/2002 | Wegerich et al. | |
| 2002/0194117 A1 | 12/2002 | Nabe et al. | |
| 2003/0023612 A1 | 1/2003 | Carlbom et al. | |
| 2003/0036903 A1 | 2/2003 | Konopka et al. | |
| 2003/0088463 A1 | 5/2003 | Kanevsky et al. | |
| 2003/0131362 A1 | 7/2003 | Jasinschi et al. | |
| 2003/0169907 A1 | 9/2003 | Edwards et al. | |
| 2003/0174773 A1 | 9/2003 | Comaniciu et al. | |
| 2004/0064341 A1 | 4/2004 | Langan et al. | |
| 2004/0095617 A1 | 5/2004 | Mangerson | |
| 2004/0147817 A1 | 7/2004 | Dewing et al. | |
| 2004/0161133 A1 | 8/2004 | Elazar et al. | |
| 2004/0174597 A1 | 9/2004 | Craig et al. | |
| 2004/0181376 A1 | 9/2004 | Fables et al. | |
| 2004/0225202 A1 | 11/2004 | Skinner | |
| 2004/0240542 A1 | 12/2004 | Yeredor et al. | |
| 2004/0249650 A1 | 12/2004 | Freedman et al. | |
| 2005/0018861 A1 | 1/2005 | Tashev | |
| 2005/0043060 A1 | 2/2005 | Brandenberg et al. | |
| 2005/0125325 A1 | 6/2005 | Chai et al. | |
| 2005/0169367 A1 | 8/2005 | Venetianer et al. | |
| 2005/0187437 A1 | 8/2005 | Matsugu et al. | |
| 2005/0216273 A1 | 9/2005 | Reding et al. | |
| 2006/0000420 A1 | 1/2006 | M Davies | |
| 2006/0004582 A1 | 1/2006 | Claudatos et al. | |
| 2006/0111961 A1 | 5/2006 | McQuivey | |
| 2006/0206379 A1 | 9/2006 | Rosenberg | |
| 2006/0251339 A1 | 11/2006 | Gokturk et al. | |
| 2007/0013776 A1 | 1/2007 | Venetianer et al. | |
| 2007/0122003 A1 | 5/2007 | Dobkin et al. | |
| 2007/0225577 A1 | 9/2007 | Mathan | |
| 2007/0230270 A1 | 10/2007 | Calhoun | |
| 2007/0291118 A1 | 12/2007 | Shu et al. | |
| 2008/0004793 A1 | 1/2008 | Horvitz et al. | |
| 2008/0004951 A1 | 1/2008 | Huang et al. | |
| 2008/0024299 A1 | 1/2008 | Robertson | |
| 2008/0031491 A1 | 2/2008 | Ma et al. | |
| 2008/0055049 A1 | 3/2008 | Weill et al. | |
| 2008/0067244 A1 | 3/2008 | Marks | |
| 2008/0071162 A1 | 3/2008 | Jaeb et al. | |
| 2008/0082399 A1 | 4/2008 | Noble et al. | |
| 2008/0092245 A1 | 4/2008 | Alward et al. | |
| 2008/0098456 A1 | 4/2008 | Alward et al. | |
| 2008/0109398 A1 | 5/2008 | Harter | |
| 2008/0228577 A1 | 9/2008 | Decre et al. | |
| 2008/0240496 A1 | 10/2008 | Senior | |
| 2008/0243439 A1 | 10/2008 | Runkle et al. | |
| 2008/0260212 A1 | 10/2008 | Moskal et al. | |
| 2008/0262743 A1 | 10/2008 | Lewis et al. | |
| 2008/0306895 A1 | 12/2008 | Karty | |
| 2008/0317292 A1 | 12/2008 | Baker et al. | |
| 2009/0002155 A1 | 1/2009 | Ma et al. | |
| 2009/0070138 A1 | 3/2009 | Langheier et al. | |
| 2009/0092283 A1 | 4/2009 | Whillock et al. | |
| 2009/0109795 A1 | 4/2009 | Marti | |
| 2009/0157481 A1 | 6/2009 | Jung et al. | |
| 2009/0164302 A1 | 6/2009 | Jung et al. | |
| 2009/0171783 A1 | 7/2009 | Raju | |
| 2009/0185723 A1 | 7/2009 | Bolle et al. | |
| 2009/0195401 A1 | 8/2009 | Maroney et al. | |
| 2009/0231436 A1 | 9/2009 | Faltesek et al. | |
| 2010/0008515 A1 | 1/2010 | Fulton et al. | |
| 2010/0131206 A1 | 5/2010 | Angell et al. | |
| 2010/0131263 A1 | 5/2010 | Angell et al. | |
| 2010/0131502 A1 | 5/2010 | Fordham | |
| 2010/0148970 A1 | 6/2010 | Angell et al. | |
| 2010/0150457 A1 | 6/2010 | Angell et al. | |
| 2010/0150458 A1 | 6/2010 | Angell et al. | |
| 2010/0153133 A1* | 6/2010 | Angell | G16H 50/20 705/3 |
| 2010/0153146 A1 | 6/2010 | Angell et al. | |
| 2010/0153147 A1 | 6/2010 | Angell et al. | |
| 2010/0153174 A1 | 6/2010 | Angell et al. | |
| 2010/0153180 A1 | 6/2010 | Angell et al. | |
| 2010/0153353 A1 | 6/2010 | Angell et al. | |
| 2010/0153389 A1 | 6/2010 | Angell et al. | |
| 2010/0153390 A1 | 6/2010 | Angell et al. | |
| 2010/0153458 A1 | 6/2010 | Angell et al. | |
| 2010/0153470 A1 | 6/2010 | Angell et al. | |
| 2010/0153597 A1 | 6/2010 | Angell et al. | |
| 2010/0177169 A1 | 7/2010 | Saric | |
| 2010/0207874 A1 | 8/2010 | Yuxin et al. | |
| 2010/0209897 A1* | 8/2010 | Utley | G09B 19/00 434/238 |
| 2012/0253207 A1* | 10/2012 | Sarkar | A61B 5/7275 600/483 |
| 2014/0139961 A1* | 5/2014 | Mellon, Jr. | H02H 5/12 361/87 |
| 2014/0228803 A1* | 8/2014 | Kogan | A61N 1/08 604/506 |
| 2015/0074431 A1* | 3/2015 | Nguyen | H02J 9/06 713/300 |
| 2015/0168976 A1* | 6/2015 | Loucks | G05B 15/02 700/287 |

OTHER PUBLICATIONS

U.S. Appl. No. 12/333,273—Final Office Action dated May 23, 2012, pp. 1-12.
U.S. Appl. No. 12/333,311—Final Office Action dated Jun. 1, 2012.
U.S. Appl. No. 12/777,122—Non-Final Office Action dated May 10, 2011.
U.S. Appl. No. 13/370,811—Specification filed Feb. 10, 2012.
U.S. Appl. No. 13/402,586—Specification filed Feb. 22, 2012.
U.S. Appl. No. 12/275,830—Notification of Allowance dated Jun. 25, 2012.
U.S. Appl. No. 13/605,248—Final Office Action dated Apr. 25, 2013.
U.S. Appl. No. 12/333,256—Final Office Action dated Jun. 26, 2013.
U.S. Appl. No. 12/333,321—Final Office Action dated Jun. 3, 2013.
U.S. Appl. No. 13/370,811—Final Office Action dated Jul. 29, 2014.
B. Hall et al., "Identifying Age, Cohort and Period Effects in Scientific Research Productivity: Discussion and Illustration Using Simulated and Actual Data on French Physicists", Jun. 26, 2005,

(56) References Cited

OTHER PUBLICATIONS

Economics of Innovation and New Technology, Taylor and Francis Journals, vol. 16 (2), pp. 1-29.
U.S. Appl. No. 12/333,273—Notice of Allowance dated Aug. 2, 2013.
U.S. Appl. No. 13/605,248—Notice of Allowance dated Aug. 26, 2013.
U.S. Appl. No. 12/333,321—Examiners Answer dated Sep. 25, 2013.
U.S. Appl. No. 12/333,311—Non-Final Office Action dated Oct. 1, 2013.
U.S. Appl. No. 12/336,488 Non-Final Office Action dated Mar. 28, 2016.
U.S. Appl. No. 12/336,440 Decision on Appeal dated Apr. 1, 2016.
U.S. Appl. No. 12/335,857 Non-Final Office Action dated Jan. 20, 2017.
U.S. Appl. No. 12/333,321 Final Office Action dated Apr. 12, 2017.
U.S. Appl. No. 12/335,521 Final Office Action dated Apr. 19, 2016.
U.S. Appl. No. 12/335,521—Decision on Appeal dated Jul. 15, 2015.
U.S. Appl. No. 12/335,857—Non-Final Office Action dated Jun. 3, 2015.
U.S. Appl. No. 12/333,256 Final Office Action dated May 17, 2017.
U.S. Appl. No. 12/333,256 Decision on Appeal dated Aug. 1, 2016.
U.S. Appl. No. 12/333,321 Decision on Appeal dated Jul. 14, 2016.
U.S. Appl. No. 12/333,321 Non-Final Office Action dated Oct. 11, 2016.
U.S. Appl. No. 12/335,521 Examiners Answer dated Oct. 18 2016.
U.S. Appl. No. 12/336,488 Final Office Action dated Nov. 18, 2016.
U.S. Appl. No. 12/333,256 Non-Final Office Action dated Dec. 1, 2016.
Lymberopoulos et al., "An Easy-To-Program Sensor System for Parsing Out Human Activities," Embedded Networks and Application Lab, Enalab, Yale University, New Haven, CT, 2008, pp. 1-17.
Girgensohn et al., "Determining Activity Patterns in Retail Spaces Through Video Analysis," MM'08, Oct. 26-31, 2008.
Yalch et al., "The Effects of Music in a Retail Setting on Real and Perceived Shopping Times," Journal of Business Research 49, pp. 139-147, 2000.
Knowledge@Wharton, Tag Team, "Tracking the Pattern of Supermarket Shoppers," Published Jun. 1, 2005.
Gulas et al., "Right Under Our Noses: Ambient Scent and Consumer Responses," Journal of Business and Psychology, Fall 1995.
M. Bitner, "The Impact of Physical Surroundings on Customer and Employees," Journal of Marketing, Apr. 1992.
Brown et al., "IBM Smart Surveillance System (S3): An Open and Extendible Architecture for Smart Video Surveillance", Retrieved on Jan. 12, 2009, pp. 1-4.
M. Borg et al., "Video Surveillance for Aircraft Activity Monitoring", IEEE Conference on Advanced Video and Signal Based Surveillance, 2005, pp. 16-21.
Y. Matsushita et al., "Illumination Normalization With Time-Dependent Intrinsic Images for Video Surveillance", IEEE Transactions on Pattern Analysis and Machine Intelligence, vol. 26, Issue 10, Oct. 2004, pp. 1336-1347.
J. Davis et al., "An Adaptive Focus-of-Attention Model for Video Surveillance and Monitoring", Machine Vision and Application 18, 2007, pp. 41-64.
L. Herbert, "Othello Error: Facial Profiling, Privacy, and the Suppression of Dissent", Ohio State Journal of Criminal Law, vol. 5, 2007, pp. 79-129.
C. Larson et al., "The Shape of Threat: Simple Geometric Forms Evoke Rapid and Sustained Rapture of Attention", Emotion 2007, vol. 7, No. 3, pp. 526-534.
A. Oredsson, "Cognitive Video Surveillance: Aan ANN/CBR Hybrid Approach", Master of Science in Informatics, Norwegian University of Science and Technology, Submitted Jun. 2007, pp. 1-136.
N. Siebel et al., "The Advisor Visual Surveillance System", Applications of Computer Vision 04, Prague, May 16, 2004, pp. 103-111.
Graham Center One-Pager, Types of Medical Errors Commonly Reported by Family Physicians, Am Fam Physician, Feb. 2003.

U.S. Appl. No. 12/333,323 Notice of Allowance dated Nov. 15, 2011.
U.S. Appl. No. 12/333,256—Non-Final Office Action dated May 23, 2011.
U.S. Appl. No. 12/333,311—Non-Final Office Action dated Jan. 24, 2012.
U.S. Appl. No. 12/275,830—Non-Final Office Action dated Dec. 14, 2011.
U.S. Appl. No. 12/333,311—Final Office Action dated Aug. 18, 2011.
U.S. Appl. No. 12/333,273—Non-Final Office Action dated Sep. 30, 2011.
U.S. Appl. No. 12/333,311—Non-Final Office Action dated Feb. 28, 2011.
U.S. Appl. No. 12/333,316—Non-Final Office Action dated Sep. 6, 2011.
U.S. Appl. No. 12/335,521—Non-Final Office Action dated Jun. 27, 2011.
U.S. Appl. No. 12/335,521—Final Office Action dated Dec. 30, 2011.
U.S. Appl. No. 12/333,319—Non-Final Office Action dated Jun. 21, 2011.
U.S. Appl. No. 12/333,319—Final Office Action dated Feb. 1, 2012.
U.S. Appl. No. 12/333,321—Non-Final Office Action dated May 23, 2011.
U.S. Appl. No. 12/335,731—Non-Final Office Action dated Oct. 26, 2011.
U.S. Appl. No. 12/336,440—Non-Final Office Action dated Jul. 21, 2011.
U.S. Appl. No. 12/336,440—Final Office Action dated Feb. 27, 2012.
U.S. Appl. No. 12/336,471—Non-Final Office Action dated Nov. 17, 2011.
U.S. Appl. No. 12/336,488—Non-Final Office Action dated Sep. 15, 2011.
U.S. Appl. No. 12/335,857—Non-Final Office Action dated Feb. 3, 2011.
U.S. Appl. No. 12/335,857—Final Office Action dated Oct. 13, 2011.
U.S. Appl. No. 12/336,488—Examiner's Answer dated Oct. 25, 2012.
U.S. Appl. No. 12/336,440—Examiner's Answer dated Nov. 23, 2012.
U.S. Appl. No. 12/333,321—Non-Final Office Action dated Dec. 19, 2012.
B. Welsh et al., "Effects of Improved Street Lighting on Crime," Sep. 24, 2008, Campbell Systematic Reviews The Campbell Collaboration, pp. 1-54.
U.S. Appl. No. 12/336,471—Notice of Allowance dated Mar. 21, 2013.
U.S. Appl. No. 12/333,273—Non-Final Office Action dated Jan. 31, 2013.
U.S. Appl. No. 12/333,259—Non-Final Office Action dated Feb. 14, 2013.
U.S. Appl. No. 14/067,300—Non-Final Office Action dated Dec. 30, 2013.
U.S. Appl. No. 13/370,811—Non-Final Office Action dated Jan. 16, 2014.
U.S. Appl. No. 14/067,300—Notice of Allowance dated Jan. 31, 2014.
U.S. Appl. No. 12/333,311—Final Office Action dated Mar. 17, 2014.
U.S. Appl. No. 12/333,256—Examiner's Answer dated Jan. 9, 2014.
U.S. Appl. No. 12/335,857—Examiner's Answer dated Mar. 15, 2012, pp. 1-17.
U.S. Appl. No. 12/336,488—Final Office Action dated Mar. 9, 2012, pp. 1-24.
U.S. Appl. No. 12/335,521—Examiner's Answer dated Apr. 25, 2012, pp. 1-9.
U.S. Appl. No. 12/33,321 Examiner's Answer dated Oct. 17, 2017.
U.S. Appl. No. 12/335,857 Final Office Action dated Oct. 19, 2017.

\* cited by examiner

CONTROLLING EQUIPMENT IN A PATIENT CARE FACILITY BASED ON NEVER-EVENT COHORTS FROM PATIENT CARE DATA

BACKGROUND

The present invention relates generally to an improved data processing system and in particular to a method and apparatus for identifying never-events. Still more particularly, the present invention relates to a computer implemented method, apparatus, and computer program product for generating never-event cohorts from a population of patients based on patient care data.

Never-events are preventable errors experienced during the provision of medical care. Never-events are characterized as clearly identifiable errors that have serious consequences for patients. In addition, the occurrence of never-events indicates a problem in the safety and credibility of a health care facility. Examples of never-events include, for example and without limitation, an unintended retention of a foreign object in a patient after surgery or other procedure; a patient death or serious disability associated with patient elopement; a patient death or serious disability associated with a medication error; a patient death or serious disability associated with an electric shock or elective cardioversion while being cared for in a healthcare facility; a patient death or serious disability associated with a fall while being cared for in a healthcare facility; a surgery performed on the wrong body part; a surgery performed on the wrong patient; a wrong surgical procedure performed on a patient; and a patient death or serious disability associated with the use of contaminated drugs.

Rules and regulations exist which require the disclosure of never-events occurring at patient care facilities. In addition, the rules and regulations, which may be instituted by medical care facilities, insurance providers, and state or federal legislation, specify various remunerative or punitive measures for the occurrence of such never-events. Consequently, interested parties may have different incentives for reporting or withholding information relating to the occurrence of never-events. For example, insurance companies may be hesitant to report the occurrence of never-events for fear of having to incur the entire cost of the medical care procedure without any patient contribution. Likewise, medical personnel may be fearful of potential repercussions for reporting the occurrence of never-events, such as pay decreases, demotions, and loss of jobs. On the other hand, patients dissatisfied with elective surgical procedures or patients who would rather not pay for costly surgical procedures may dishonestly claim that they have suffered from never-events in an attempt to avoid payment.

SUMMARY

In an embodiment of the present invention, a computer implemented method modifies a unit of medical equipment based on never-event cohorts, where a never-event is a preventable error experienced by a patient while receiving medical care. One or more processors, in response to receiving patient care data derived from a population of patients, processes the patient care data to form digital patient care data, where the digital patient care data includes metadata describing a set of patient care patterns associated with one or more patients in the population of patients, and where the set of patient care patterns is one or more patterns of events that indicate a likely occurrence of a never-event at a patient care facility. The processor(s) analyze the digital patient care data using cohort criteria to identify a set of never-event attributes from the set of patient care patterns. The never-event attributes do not directly describe a never-event, the cohort criteria specify at least one never-event attribute from the set of never-event attributes for each cohort in a set of never-event cohorts, and the never-event attributes identify common medical care procedures given to each cohort member. The processor(s) receive, from a set of sensors, facility event data. The set of sensors include one or more of a motion sensor, a temperature sensor, a video camera, and a microphone capturing the facility event data. The facility event data describes environmental conditions within a patient care facility, the facility event data is a component of patient care data, and the patient care data includes the set of patient care patterns. The processor(s) form new digital patient care data from the patient care data, and generate the set of never-event cohorts comprising members selected from the population of patients, where each member of a cohort in the set of never-event cohorts has the at least one never-event attribute in common, where the set of sensors detect an electrical fault in a unit of medical equipment used on patients in the patient care facility, where the electrical fault causes an unwanted electrical shock to a user of the unit of medical equipment, and where the unwanted electrical shock is the never-event at the patient care facility. The processor(s) modify the unit of medical equipment in order to correct the electrical fault.

In an embodiment of the present invention, a computer program product is executable to restore power to a patient care facility based on never-event cohorts, where a never-event is a preventable error experienced by a patient while receiving medical care. The computer program product comprises: a non-transitory computer recordable-type medium; first program instructions for processing patient care data derived from a population of patients to form digital patient care data in response to receiving the patient care data, where the digital patient care data comprises metadata describing a set of patient care patterns associated with one or more patients in the population of patients, and where the set of patient care patterns is one or more patterns of events that indicate a likely occurrence of a never-event at a patient care facility; second program instructions for analyzing the digital patient care data using cohort criteria to identify a set of never-event attributes from the set of patient care patterns, where the never-event attributes do not directly describe a never-event, where the cohort criteria specifies at least one never-event attribute from the set of never-event attributes for each cohort in a set of never-event cohorts, and where the never-event attributes describe common medical care procedures given to each cohort member; third program instructions for receiving, from a set of sensors, facility event data, where the set of sensors comprises a motion sensor, a temperature sensor, a video camera, a power sensor, and a microphone capturing the facility event data, where the facility event data describes environmental conditions within a patient care facility, where the power sensor detects a lack of power in the patient care facility, where the facility event data is a component of patient care data, and where the patient care data comprises the set of patient care patterns; fourth program instructions for forming new digital patient care data from the patient care data; fifth program instructions for generating the set of never-event cohorts comprising members selected from the population of patients, where each member of a cohort in the set of never-event cohorts has the at least one never-event attribute in common; sixth program instructions for transmitting an instruction, based on the set of never-event cohorts, to a power controller to restore power to the patient care facility, where the never-event at the patient care facility is an interruption of power to the patient care facility. The first program instructions, the second program instructions, the third program instructions, the fourth program instructions, the fifth program instructions, and the sixth program instructions are stored on the non-transitory computer recordable-type medium.

In an embodiment of the present invention, an apparatus restores power to a patient care facility based on never-event cohorts, where a never-event is a preventable error experienced by a patient while receiving medical care. The apparatus includes: a bus system; a memory connected to the bus system, where the memory includes computer usable program code; and a processing unit connected to the bus system, where the processing unit executes the computer usable program code to: process patient care data derived from a population of patients to form digital patient care data in response to receiving the patient care data, where the digital patient care data comprises metadata describing a set of patient care patterns associated with one or more patients in the population of patients, and where the set of patient care patterns is one or more patterns of events that indicate a likely occurrence of a never-event at a patient care facility; analyze the digital patient care data using cohort criteria to identify a set of never-event attributes from the set of patient care patterns, where the never-event attributes do not directly describe a never-event, and where the cohort criteria specify at least one never-event attribute from the set of never-event attributes for each cohort in a set of never-event cohorts, and where the never-event attributes describe common medical care procedures given to each cohort member; receive, from a set of sensors, facility event data, where the set of sensors comprises a motion sensor, a temperature sensor, a video camera, a power sensor, and a microphone capturing the facility event data, where the facility event data describes environmental conditions within a patient care facility, where the power sensor detects a lack of power in the patient care facility, where the facility event data is a component of patient care data, and where the patient care data comprises the set of patient care patterns; form new digital patient care data from the patient care data; generate the set of never-event cohorts comprising members selected from the population of patients, where each member of a cohort in the set of never-event cohorts has the at least one never-event attribute in common; and transmit an instruction, based on the set of never-event cohorts, to a power controller to restore power to the patient care facility, where the never-event at the patient care facility is an interruption of power to the patient care facility.

The described embodiments of the present invention may also be implemented as a method, a computer system, and/or as a computer program product, if not already described as such.

DETAILED DESCRIPTION

Figure 1:
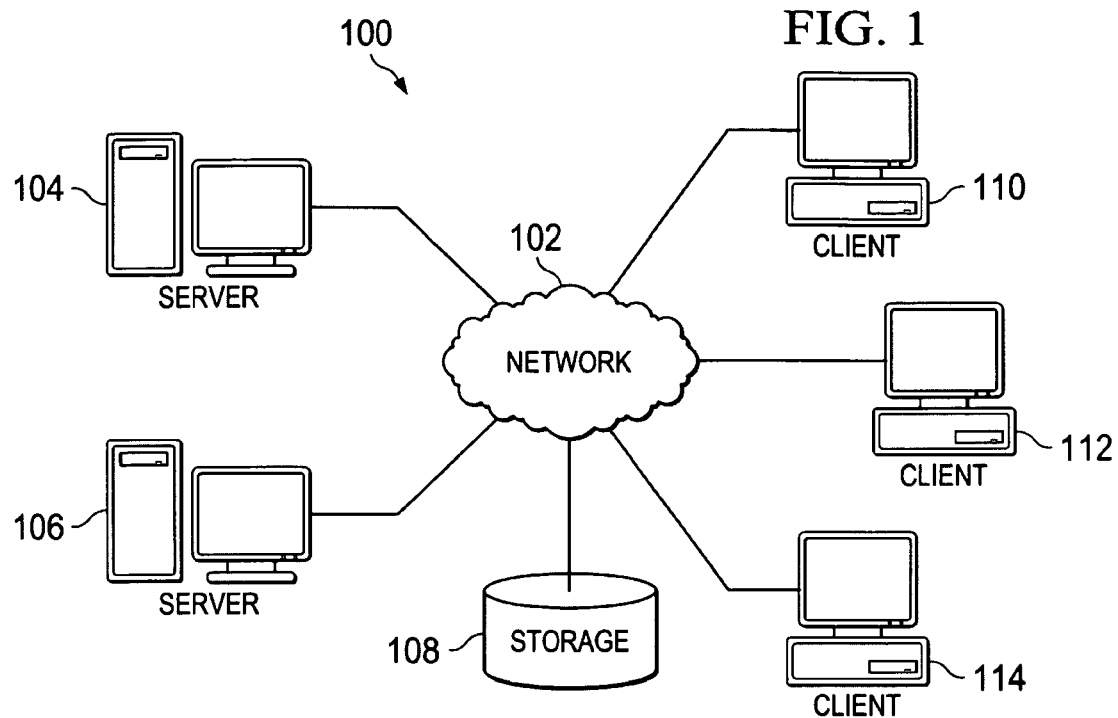
FIG. 1 is a pictorial representation of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device.

Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
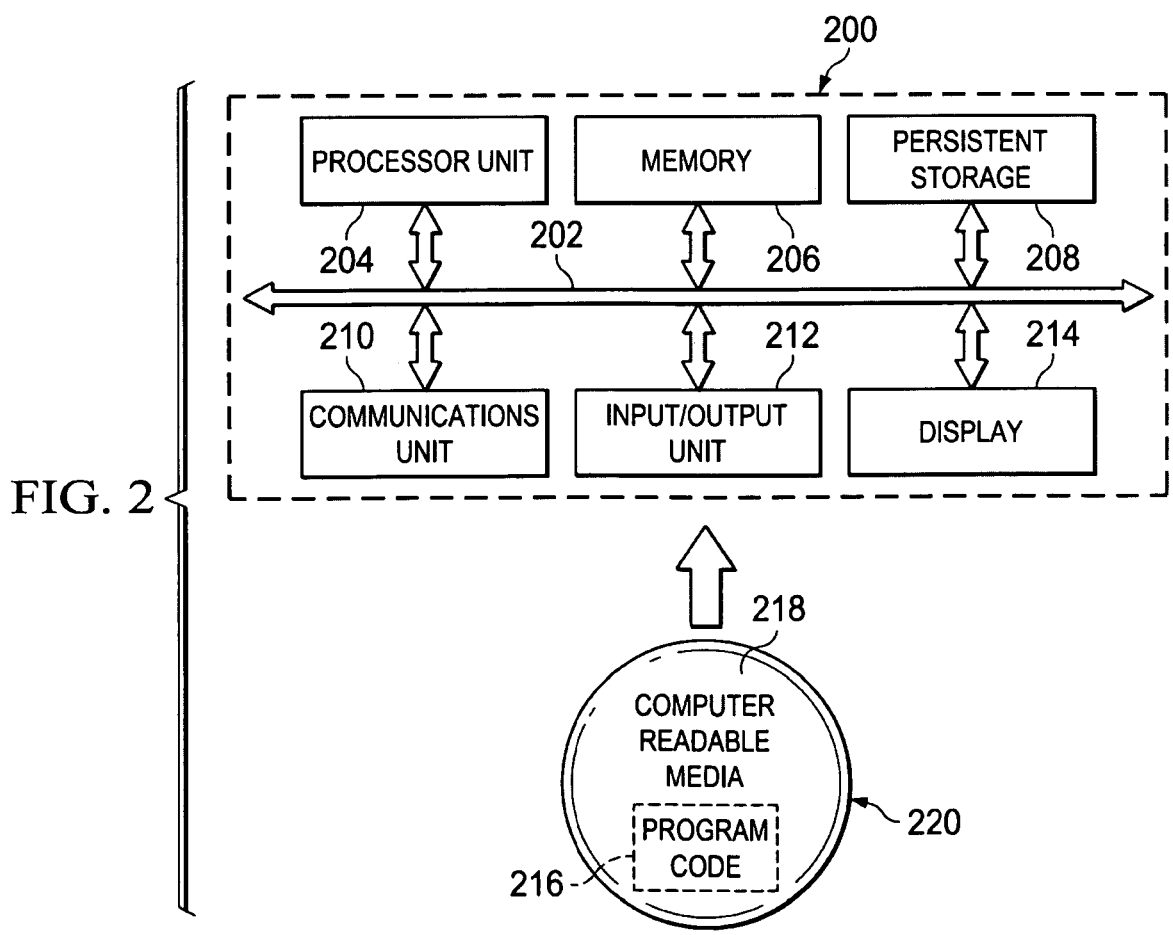
FIG. 2 is a block diagram of a data processing system in which illustrative embodiments may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In an illustrative example, a client computer, such as client 110, may host a never-event pattern processing engine and a cohort generation engine for generating a set of never-event cohorts. The never-event cohorts may be formed from patient care data for one or more patients from a population of patients at one or more treatment facilities. A population of patients refers to one or more patients. The population of patients may be a population of patients at a medical facility, patients being treated at home or in a managed care facility, patients in out-patient care, or a combination of patients at a medical facility and patients that are not being treated in a medical facility. The population of patients may also include patients at a single medical facility or patients at two or more medical facilities. The never-event cohorts may be generated from patient care data that is formed from at least one of facility event data and medical records. As used herein, the term "at least one of", when used with a list of items means that different combinations of one or more of the items may be used and only one of each item in the list may be needed. For example, "at least one of item A, item B, and item C" may include, for example, without limitation, item A, or item A and item B. This example also may include item A, item B, and item C, or item B and item C. Thus, the never-event cohorts may be generated from facility event data, medical records, or both facility event data and medical records.

In addition, the client computer may also host an inference engine for generating inferences related to the set of never-event cohorts. The inferences drawn from the set of never-event cohorts may indicate, for example, likely causes of the never-event, the likelihood of the never-event occurring in the absence of culpable action or inaction, whether or not the patient contributed to the never-event, or whether preventative measures could have or should have prevented the occurrence of the never-event.

Program code located in network data processing system 100 may be stored on a computer recordable storage medium and downloaded to a data processing system or other device for use. For example, program code may be stored on a computer recordable storage medium on server 104 and downloaded to client 110 over network 102 for use on client 110.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

In some illustrative embodiments, program code 216 may be downloaded over a network to persistent storage 208 from another device or data processing system for use within data processing system 200. For instance, program code stored in a computer readable storage medium in a server data processing system may be downloaded over a network from the server to data processing system 200. The data processing system providing program code 216 may be a server computer, a client computer, or some other device capable of storing and transmitting program code 216.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

Patient care data is data associated with the provision of medical care to one or more patients from a population of patients. Thus, patient care data may be event data generated during the rendering of medical care to one or more patients in a population of patients. The event data may be collected by a set of sensors distributed throughout a patient care facility. The sensors may monitor patients, medical personnel, tools and equipment, environmental conditions at a patient care facility, or from any other person, place, or object. In some instances, patient care data may originate from medical records filled out by patients and/or medical personnel, from insurance applications, or any other source of medical-related information. Cohorts may be formed from patient care data for identifying patients who have likely experienced never-events.

Cohorts are often generated based upon the selection of one or more attributes shared by members of the cohort. The information used to identify the attributes of members of the cohort is typically provided by the members of the cohort. However, this information may be voluminous, dynamically changing, unavailable, and/or unknown to the members of the cohort, or the entity selecting members of a cohort group. Moreover, it may be difficult, time consuming, or impractical for an entity to access all the information necessary to accurately generate cohorts. In addition, unique cohorts are typically sub-optimal because cohort creators lack the skills, time, knowledge, and/or expertise needed to gather cohort attribute information from available sources. In addition, reporting entities may be hesitant to provide the requisite information if the result of such reporting may result in negative consequences.

The illustrative embodiments disclosed herein recognize that patient care data formed from medical records and event data collected by a set of sensors deployed at a patient care facility can be used to generate a set of never-event cohorts populated with members sharing common attributes. The common attributes may be, for example, a common surgical procedure that was performed, a type of medical device that was used in a surgical procedure, a common medical care facility protocol instituted for patients, or any other type of attribute. In the illustrative embodiments disclosed herein, members of a cohort are preferably humans; however, in alternate embodiments, other living organisms, such as animals, may be members of a never-event cohort. Cohorts may be used in research, marketing, safety studies, and many other various uses.

Therefore, in one embodiment of the present invention, a computer implemented method, apparatus, and computer program product is provided for generating never-event cohorts. A never-event cohort is a group of members who share one or more common attributes as defined or selected by cohort criteria. The common attributes may be identified from a set of patient care patterns present in patient care data that is either captured by a set of sensors or present in medical records or other sources of medical information. As used herein, the term "set" may refer to one or more. Thus, a set of sensors may be a set formed from a single sensor, or two or more sensors.

The set of sensors deployed in a patient care facility captures facility event data which may be processed to identify a set of never-event patterns. The facility event data, which is captured in an analog format, is processed and transformed into a digital format for use in a cohort generation engine. The cohort generation engine receives the digital facility event data and generates a set of never-event cohorts from never-event attributes formed from never-event patterns in accordance with cohort criteria. In one embodiment, the never-event cohorts may be used in a system-wide monitoring process to quickly and efficiently pass vital information to a real-time computational process. Thus, the embodiments described herein permit a user to create never-event cohorts based on patient care data for a population of patients. Never-event cohorts are groups of members who are selected based upon one or more common attributes. Examples of attributes include, for example, a type of surgical procedure, a type of antibiotics administered, equipment used, age, gender, weight, or any other attribute.

The illustrative embodiments described herein provide a computer implemented method, apparatus, and computer program product for generating never-event cohorts. In one embodiment, in response to receiving patient care data derived from a population of patients, the patient care data is processed to form digital patient care data. The digital patient care data includes metadata describing a set of patient care patterns associated with one or more patients in the population of patients. The digital patient care data is analyzed using cohort criteria to identify a set of never-event attributes from the set of patient care patterns. The cohort criteria specify at least one never-event attribute from the set of never-event attributes for each cohort in a set of never-event cohorts. Thereafter, a set of never-event cohorts is generated. The set of never-event cohorts is formed from members selected from the population of patients, and each member of a cohort in the set of never-event cohorts has the at least one never-event attribute in common.

Figure 3:
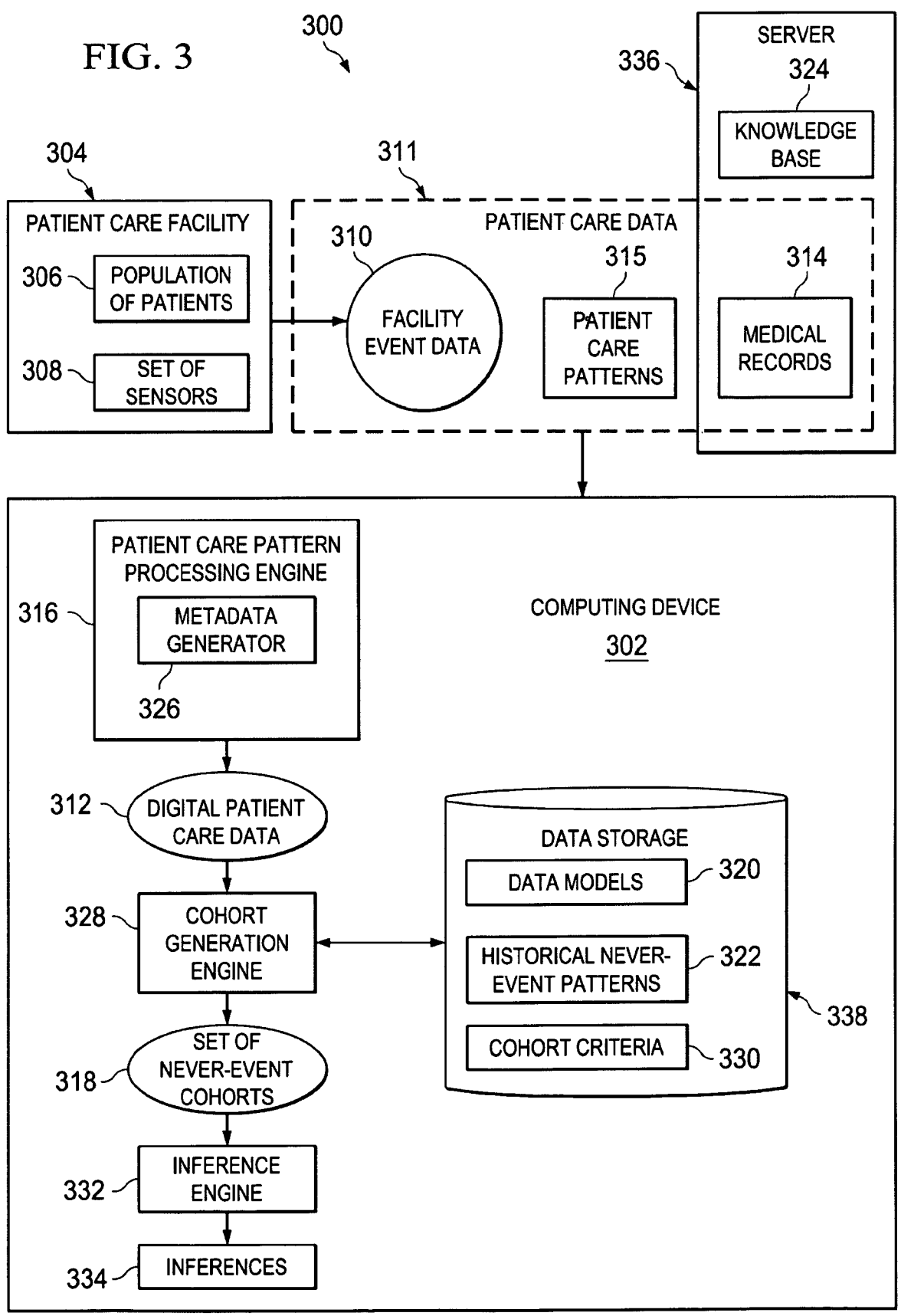
FIG. 3 is a block diagram of a data processing system for generating never-event cohorts in accordance with an illustrative embodiment.

FIG. 3 is a block diagram of a data processing system for generating never-event cohorts in accordance with an illustrative embodiment. Data processing system 300 is a data processing system, such as data processing system 100 in FIG. 1. In addition, computing device 302 of data processing system 300 may be implemented using any type of computing device, including but not limited to, a main frame, a server, a personal computer, a laptop, a personal digital assistant (PDA), or any other computing device depicted in FIGS. 1 and 2.

Patient care facility 304 is one or more facilities in which medical care is provided. Examples of patient care facility 304 may include, without limitation, a hospital, a nursing home, an assisted living center, an emergency room, a dental office, an ambulance, or a clinic. In addition, patient care facility 304 may be formed from one or more hospital systems located in different geographic locations. In another example, patient care facility 304 is any location in which medical care is provided to one or more patients. Thus, for example, a patient receiving emergency medical treatment at an accident site or in a restaurant would still be receiving medical treatment at patient care facility 304.

Medical care is provided to population of patients 306. Population of patients 306 is a group of patients receiving medical care at patient care facility 304. Thus, population of patients 306 includes every patient receiving treatment regardless of the type of medical care received.

Patient care facility 304 includes set of sensors 308. Set of sensors 308 is one or more sensors for capturing facility event data 310 originating from patient care facility 304. Set of sensors 308 may include, for example, pressure sensors, motion sensors, temperature sensors, patient monitoring devices, video cameras, microphones, or any other type of device for capturing facility event data 310. In this example in FIG. 3, set of sensors 308 is implemented as a separate device than computing device 302. However, in other embodiments, set of sensors 308 may be embodied with computing device 302 within a single device.

Facility event data 310 is data captured at a patient care facility, such as patient care facility 304, by set of sensors 308. Facility event data 310 is data gathered from the monitoring of people, plants, animals, conditions, or locations at patient care facility 304. Facility event data 310 includes, for example and without limitation, environmental event data, care management event data, patient protection event data, surgical event data, device event data, or any other type of event data that may be collected from patient care facility 304. Examples of event data that form facility event data 310 are discussed in more detail in FIG. 4.

Facility event data 310 is a component of patient care data 311. Patient care data 311 is data derived from and/or describing medical care received by patients. In addition, patient care data 311 includes information contained within or derived from medical records 314. Medical records 314 are records documenting the medical history and care of a population of patients, such as population of patients 306. In other embodiments, patient care data 311 may include other sources of information relating to the medical history and care of patients. For example, patient care data 311 may include information originating from insurance records, job application forms, orphanages, or any other source of patient care information.

Over time, as patient care data 311 is aggregated, patient care patterns 315 become detectable. Patient care patterns 315 are patterns of data present in patient care data 311 that relate to the provision of medical care to population of patients 306. For example, a patient care pattern in patient care patterns 315 may indicate a protocol followed by medical care providers in an emergency room for patients suffering from lacerations. Another patient care pattern may describe the manner in which nurses at a hospital respond to patients' request for assistance, or how patients in a hospital recover from surgery performed using a particular medical device. Yet another patient care pattern from patient care patterns 315 may show the manner in which hospital food is prepared, or the manner in which psychiatric patients are restrained to prevent self-injury.

Patient care patterns 315 are detected in patient care data 311 by patient care pattern processing engine 316. Patient care pattern processing engine 316 is a software component for processing patient care data 311 to form digital patient care data 312. Digital patient care data 312 is patient care data 311 that has been processed and converted, if necessary, into digital format usable for generating set of never-event cohorts 318. For example, facility event data 310 may be captured by set of sensors 308 in analog format. Thus, facility event data 310 may require conversion into digital format to be compatible with other software components for generating set of never-event cohorts 318. In addition, components of patient care data 311 which are already in digital format may still require the addition of metadata tags which are provided in the processing of patient care data 311.

Patient care pattern processing engine 316 includes metadata generator 326. Metadata generator 326 is a software component for generating metadata tags for identifying patient care patterns 315. In one embodiment, metadata generator 326 generates metadata tags describing the data in patient care data 311. Thereafter, patient care pattern processing engine 316 references the metadata tags for identifying patient care patterns 315. Once identified, individual patient care patterns from patient care patterns 315 may also serve as attributes upon which set of never-event cohorts 318 may be based.

The processing of patient care data 311 by patient care pattern processing engine 316 identifies patient care patterns 315 from patient care data 311. In one embodiment, patient care pattern processing engine 316 identifies the set of never-event patterns from patient care data 311 by processing patient care data 311 and any associated metadata tags generated by metadata generator 326 in data models 320. Data models 320 is a set of one or more data models for processing patient care data 311 for identifying patient care patterns 315 that may then be used to form attributes for generating set of never-event cohorts 318. A data model is a model for structuring, defining, organizing, imposing limitations or constraints, and/or otherwise manipulating data or metadata to produce a result. A data model may be generated using any type of modeling method or simulation including, but not limited to, a statistical method, a data mining method, a causal model, a mathematical model, a marketing model, a behavioral model, a psychological model, a sociological model, or a simulation model.

Data models 320 may be used to identify patterns of medical care that were statistically likely to be the result of a never-event. For example, patient care pattern processing engine 316 may reference data models 320 to determine that patients who received treatment consistent with a head injury, despite the fact that the patient was admitted to patient care facility 304 for an unrelated medical procedure, had suffered a never-event within a statistical measure of probability. If desired, thereafter, the occurrence of a suspected never-event may be investigated at patient care facility 304 to confirm whether or not the head injury was related to the original scope of medical care or if the injury was, in fact, a never-event.

In another embodiment, patient care pattern processing engine 316 identifies the set of never-event patterns by comparing patient care data 311, including any metadata tags generated by metadata generator 326, to historical never-event patterns 322. Historical never-event patterns 322 is a set of one or more never-event patterns encountered over time at patient care facility 304. Patient care pattern processing engine 316 may analyze patient care data 311 to never-event attributes by comparing patient care patterns 315 with historical never-event patterns 322. The comparison of patient care patterns 315 to historical never-event patterns 322 enables patient care pattern processing engine 316 to identify never-event attributes based on the never-event attributes associated with historical never-event patterns 322. Once identified, the attributes derived from historical never-event patterns 322 may be associated with patient care patterns 315 from patient care data 311.

Never-event patterns may also be identified by patient care pattern processing engine 316 by comparing facility event data 310 with known information and expected protocols that are specified in knowledge base 324. Knowledge base 324 is a collection of facts, criteria, factors, and other information that may be used for, among other things, identifying never-event patterns. Failure to conform to protocols specified in knowledge base 324 may result in the identification of never-event patterns.

Patient care pattern processing engine 316 sends digital patient care data 312 to cohort generation engine 328 for generating set of never-event cohorts 318. Set of never-event cohorts 318 is a group of patients from population of patients 306 having one or more common never-event attributes. Set of never-event cohorts 318 is generated from patient care data 311 that has been processed to form digital patient care data 312. Examples of never-event cohorts included in set of never-event cohorts 318 may include, for example, patients who have received a surgical procedure, but not suffered a never-event. Another never-event cohort from set of never-event cohorts 318 may include patients who have received a surgical procedure, but experienced a pattern of events that indicates a never-event may have occurred. Further, this cohort of patients may include sub-cohorts based on the type of never-event to which patients were exposed. For example, one sub-cohort may include patients who suffered from medical equipment left inside their body, whereas a second sub-cohort may include patients who received the wrong blood type during surgery.

Cohort generation engine 328 is a software program that generates set of never-event cohorts 318 from digital patient care data 312. In an alternate embodiment, cohort generation engine 328 may request digital patient care data 312 from a data storage device where digital patient care data 312 is stored. In other embodiments, patient care pattern processing engine 316 may automatically send digital patient care data 312 to cohort generation engine 328 in real time, as digital patient care data 312 is generated. In addition, another embodiment may have patient care pattern processing engine 316 send digital patient care data 312 to cohort generation engine 328 upon the occurrence of a predetermined event. The predetermined event may be the expiration time; the completion of a task, such as processing patient care data 311; the occurrence of a timeout event; a user request; or any other predetermined event. Thus, the illustrative embodiments may utilize digital patient care data 311 in real time as digital patient care data 311 is generated. The illustrative embodiments may also utilize digital patient care data 311 that is pre-generated and/or stored in a data storage device until the digital patient care data is retrieved at some later time.

Cohort generation engine 328 generates set of never-event cohorts 318 with reference to never-event attributes described by metadata provided by metadata generator 326. In addition, cohort generation engine 328 references cohort criteria 330 in generating set of never-event cohorts 318. Cohort criteria 330 is a set of criteria and/or guidelines for generating set of never-event cohorts 318. Cohort criteria 330 specifies a grouping of members into cohorts based upon predefined attributes such as, for example, the patients age, the medical procedure performed, the drugs administered, the outcome of patient care, or the exposure to one or more never-events. For example, cohort criteria 330 may specify that a particular cohort group included in set of never-event cohorts 318 should include all patients who have received a surgical procedure on the wrong body part.

In one embodiment, cohort generation engine 328 provides set of never-event cohorts 318 to inference engine 332. Inference engine 332 is a software component, such as a computer program, that derives inferences 334 based upon input, such as set of never-event cohorts 318. Inferences 334 are conclusions regarding possible future events or future changes in the attributes of cohorts that are drawn or inferred. Inferences 334 are derived in accordance with knowledge base 324. Knowledge base 324 is depicted as being stored in server 336; however, in other embodiments, knowledge base 324 may be stored in computing device 302 or any other data storage device, such as data storage 338. Data storage 338 is a device for storing data. Data storage 338 may be, for example, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media; such as those supporting the Internet or an intranet, or a magnetic storage device. In an alternate embodiment, data storage 338 may be located in a remote location accessible to computing device 302 via a network, such as network 102 in FIG. 1.

For example, set of never-event cohorts 318 may be analyzed by inference engine 332 to identify a source or cause of a never-event. For example, inference engine 332 may receive set of never-event cohorts 318 including patients who have received any type of surgical procedure, but who share the common attribute of having contracted a hospital-borne infection. Inference engine 332 may generate inferences 334 that initially indicate that the cohort members are suffering from a hospital-borne infection based upon patient care data 311. Inference engine 332 may then identify a source of the infection, such as a particular patient from which the infection originated based upon, for example, the manner in which the infection spread among members of the cohort, or inference engine 332 may infer the manner in which the infection was passed. In addition, inference engine 332 may identify the type of infection based upon, for example, symptoms experienced by patients.

Figure 4:
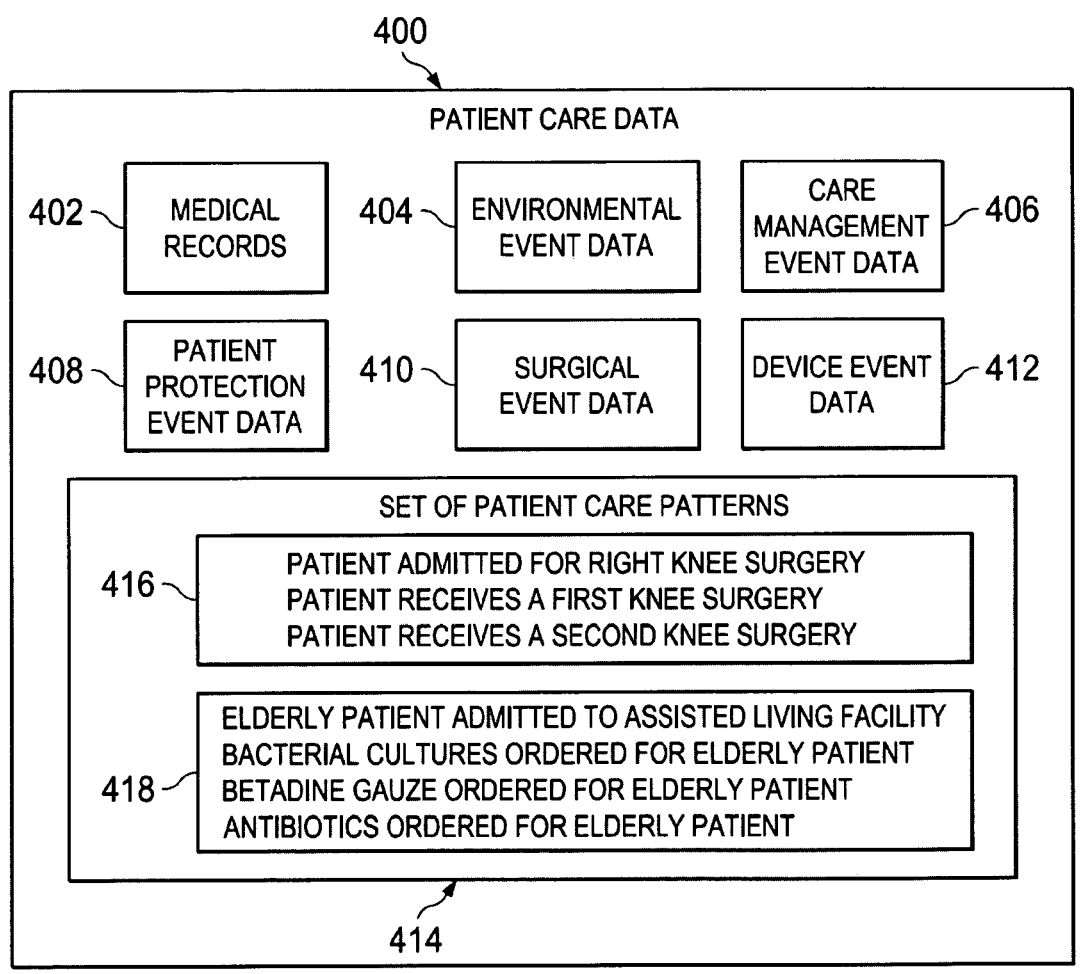
FIG. 4 is a block diagram of patient care data used for generating never-event cohorts in accordance with an illustrative embodiment.

FIG. 4 is a block diagram of patient care data used for generating never-event cohorts in accordance with an illustrative embodiment. Patient care data 400 is patient care data, such as patient care data 311 in FIG. 3.

Patient care data 400 includes information collected from medical records 402. Medical records 402 are medical records, such as medical records 314 in FIG. 3. In addition, patient care data 400 includes event data that may be derived from facility event data, such as facility event data 310 in FIG. 3. Examples of event data included in patient care data 400 include environmental event data 404. Environmental event data 404 is data describing environmental events or conditions in a patient care facility. For example, environmental event data 404 may include, without limitation, data describing the existence of infectious bacteria in operating rooms or recovery rooms, the lack of power in a medical care facility, electrical shocks surging through equipment, temperatures, the number and location of healthcare professionals in a medical care facility, or other environmental factors. As such, if the set of sensors 308 shown in FIG. 3 detect an electrical fault in a unit of medical equipment that is used on patients in the patient care facility 304, where the electrical fault causes an unwanted electrical shock to a user of the unit of medical equipment, and the unwanted electrical shock is the never-event at the patient care facility, then one or more processors in computing device 302 will send an instruction to a power controller in the faulty unit of medical equipment to turn off power going to that faulty unit of medical equipment, thus correcting the electrical fault by simply removing the power supply to that faulty unit of medical equipment. In another embodiment of the present invention, if the power controller is actually controlling a power source to all of the patient care facility 304, and the set of sensors 308 send the computing device 302 a signal indicating that the entire patient care facility has lost power (i.e., experienced an interruption of power) from a primary power source (e.g., a municipal power grid), then the computing device 302 will send a signal to the power controller to switch to a secondary power supply (e.g., a backup generator), thereby providing (restoring) power to the patient care facility 304.

Patient care data 400 may also include care management event data 406. Care management event data 406 is data describing events pertaining to care management received by a patient in a patient care facility. Care management event data 406 may describe, for example, a type, an amount, a rate, or a method of administration of a drug; a type of medical procedure performed on a patient; the frequency of which a nurse assists patients; the frequency of which a doctor sees patients; the type of postoperative care received by a patient; or any other conditions or events related to the care of patients in a medical care facility.

Patient protection event data 408 may also be included in patient care data 400. Patient protection event data 408 is data describing events or conditions in a medical care facility relating to patient safety in a medical care facility. For example, patient protection event data 408 may describe the release of a newborn infant to an adult. The identity of the adult may be determined from patient care facility records, such as medical records 402, or from event data collected by a set of sensors at a patient care facility. For example, set of sensors 308 in FIG. 3, which are deployed in patient care facility 304 in FIG. 3, may use digital video cameras and facial recognition software for identifying infants and adults to whom the infants are released. Patient protection event data 408 may also include data describing when and for how long a patient may have been missing, or whether or not the patient has self-inflicted injuries and is in need of restraint.

Patient care data 400 may also include surgical event data 410. Surgical event data 410 is data relating to the performance of surgeries on patients in a patient care facility. Surgical event data 410 may describe, for example and without limitation, a body part on which surgery is performed, an identity of the patient receiving the surgery, the type of procedure to be performed, the type of equipment used, whether equipment was inadvertently left inside a patient, or other categories of event data relating to surgical events in a patient care facility.

Device event data 412 may also be included in patient care data 400. Device event data 412 is data describing the use of devices in a patient care facility. For example, patient care data 400 may describe the existence and use of contaminated drugs, devices, or biologics provided by a patient care facility; or the manner of the use or function of a device in providing medical care in which the device is used or functions other than as intended; or other event data describing the use or condition of devices in a patient care facility.

Patient care data 400 may be formed from medical records for every patient in a population of patients receiving medical care at a medical care facility. In addition, patient care data 400 may be formed from event data captured at a medical care facility, such as facility event data 310 in FIG. 3. Patient care data 400 may be processed to identify set of patient care patterns 414. Set of patient care patterns 414 is one or more patterns of events that indicate the likely occurrence of a never-event at a patient care facility. For example, patient care data 400 may include pattern of events 416. Pattern of events 416 is a sequence of one or more events or conditions for one or more patients derived from either the patients' medical records or from facility event data captured by a set of sensors at a patient care facility in which the patients received medical care. The repeated occurrence of the events in pattern of events 416 for one or more patients in a population of patients yields a pattern of events which is recognizable by a never-event pattern processing engine, such as patient care pattern processing engine 316 in FIG. 3. Once identified, the pattern processing engine is capable of determining the probability that a never-event occurred.

In this example in FIG. 4, pattern of events 416 is an example of a pattern of events describing medical care received by a patient admitted to a patient care facility for surgery on the patient's right knee. After admittance, the patient receives a first knee surgery, and then the patient receives a second knee surgery. In this illustrative example, pattern of events 416 was derived from at least one of the medical records or the facility event data. In other words, pattern of events 416 may have been derived solely from medical records 402, solely from event data captured at a patient care facility, or from a combination of medical records 402 and event data captured at a patient care facility. Pattern of events 416 may indicate the occurrence of a never-event. In particular, pattern of events 416 may indicate that a medical procedure was performed on the wrong body part because two knee surgeries were performed on a patient who was admitted for a single surgery on the right knee.

Metadata describing the events in pattern of events 416 may be generated by a metadata generator, such as metadata generator 326 in FIG. 3, and incorporated into digital patient care data. The digital patient care data may then be used for generating a set of never-event cohorts.

In addition, set of patient care patterns 414 includes pattern of events 418. Pattern of events 418 is a pattern of events describing medical care received by an elderly patient at a patient care facility. Pattern of events 418 indicates that the elderly patient had been admitted to an assisted living facility. In addition, pattern of events 418 indicates that the elderly patient had been ordered bacterial cultures, betadine gauze, and antibiotics. The pattern of events described in pattern of events 418 is consistent with treatment for pressure sores, a commonly experienced never-event. Thus, although a single event may not have been sufficient to identify a never-event, a pattern of events, such as pattern of events 418, may indicate the occurrence of a never-event.

As disclosed above, metadata describing the events in pattern of events 418 may be generated by a metadata generator, and incorporated into digital patient care data. The digital patient care data may then be used for generating a set of never-event cohorts, such as set of never-event cohorts 318 in FIG. 3.

Figure 5:
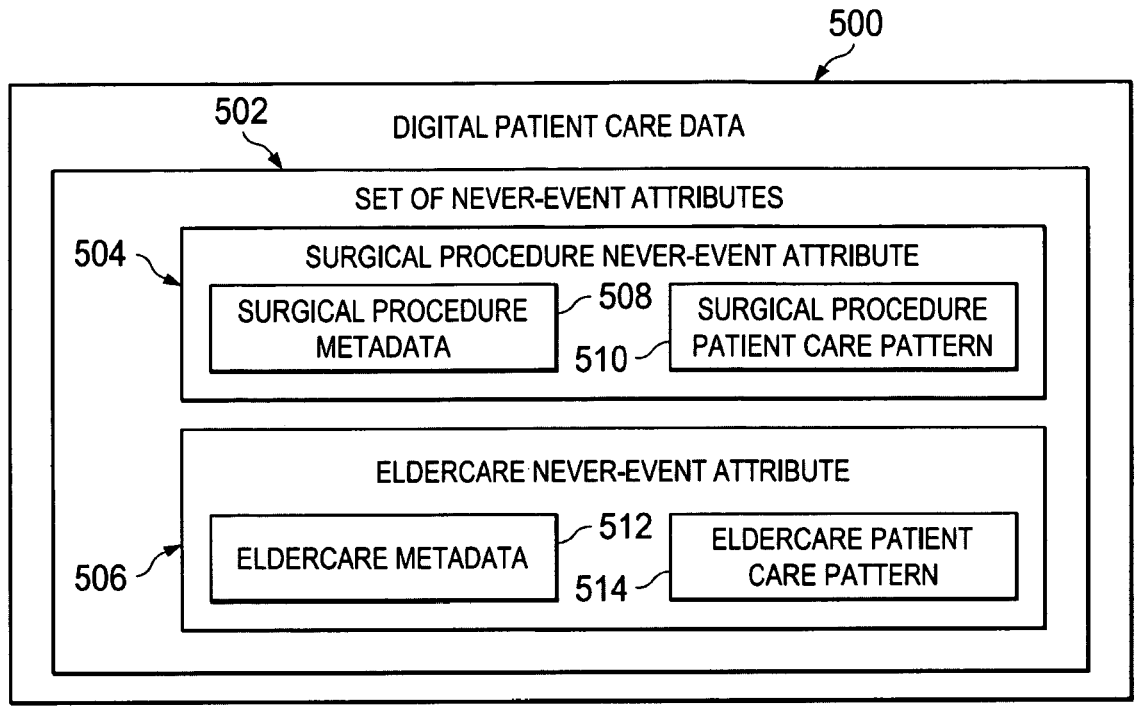
FIG. 5 is a block diagram of digital patient care data in accordance with an illustrative embodiment.

FIG. 5 is a block diagram of digital patient care data in accordance with an illustrative embodiment. Digital patient care data 500 is digital patient care data, such as digital patient care data 312 in FIG. 3. Processing of digital patient care data 500 generates set of never-event attributes 502. Set of never-event attributes 502 is a set of one or more attributes upon which a never-event cohort may be based.

Set of never-event attributes 502 includes surgical procedure never-event attribute 504 and eldercare never-event attribute 506. In an illustrative embodiment, set of never-event attributes 502 are identified by a cohort generation engine, such as cohort generation engine 328 in FIG. 3, with reference to cohort criteria.

In one embodiment, surgical procedure never-event attribute 504 is a never-event attribute identified from surgical procedure metadata 508. Surgical procedure metadata 508 is metadata generated by a metadata generator for describing surgical procedure patient care pattern 510. Surgical procedure patient care pattern 510 is a set of one or more patient care patterns derived from facility event data, medical records, and/or other sources of patient care information. Thus, surgical procedure patient care pattern 510 may include data and information generated from a time before, during, and after the surgical procedure, and may describe the preparation taken, the surgical operation performed, and postoperative care given Similarly, eldercare never-event attribute 506 is a never-event attribute identified from eldercare metadata 512 generated by a metadata generator for describing eldercare patient care pattern 514. Eldercare patient care pattern 514 is a set of one or more patient care patterns derived from facility event data, medical records, and/or other sources of patient care information. In particular, Eldercare patient care pattern 514 is derived from the provision of eldercare services to elderly patients at a patient care facility. For example, eldercare patient care pattern 514 may describe the schedule at which elderly patients are fed, the type of food provided, and the amount of food provided. Eldercare patient care pattern 514 may describe types and amounts of medication provided to elderly patients, or any other type of patient care being provided.

Figure 6:
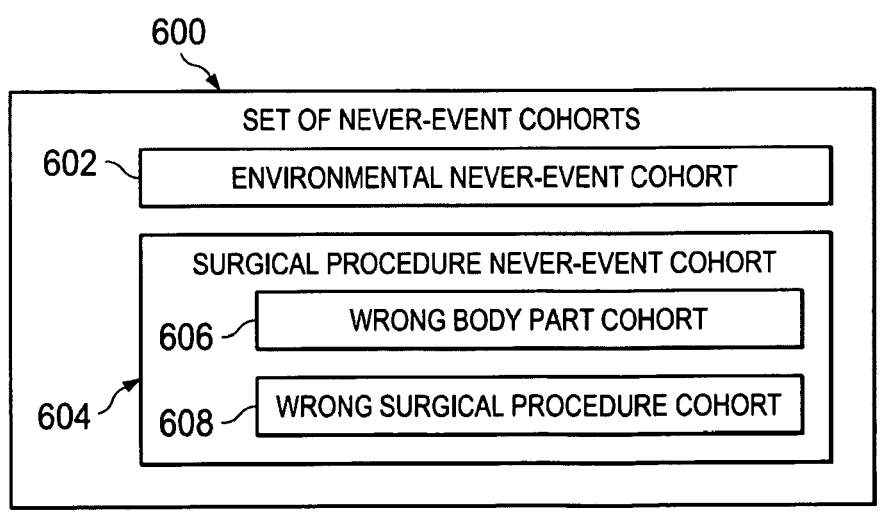
FIG. 6 is a block diagram of a set of never-event cohorts in accordance with an illustrative embodiment.

FIG. 6 is a block diagram of a set of never-event cohorts in accordance with an illustrative embodiment. Set of never-event cohorts 600 is a set of never-event cohorts, such as set of never-event cohorts 318 in FIG. 3.

Set of never-event cohorts 600 includes environmental never-event cohort 602. Environmental never-event cohort 602 is a cohort formed of members selected from a population of patients, such as population of patients 306 in FIG. 3. Environmental never-event cohort 602 is one or more cohorts based on environmental never-event attributes. An environmental never-event attribute is a never-event attribute formed from patterns of patient care describing the environmental conditions and events during the provision of patient care. Thus, members of environmental never-event cohort 602 are grouped according to environmental never-event attributes experienced. For example, a cohort in environmental never-event cohort 602 may include members of a population of patients who have suffered from an electric shock while being cared for in a healthcare facility. Another cohort may include members who were given a line designated for oxygen or other gas to be delivered to a patient which contained the wrong gas or was contaminated by toxic substances. Similarly, other cohorts may include members who have suffered a burn, or other injuries resulting from environmental conditions and events at a patient care facility.

Surgical procedure never-event cohort 604 is a cohort of set of never-event cohorts 600 including two cohorts. In particular, surgical procedure never-event cohort 604 is a cohort having members who have suffered surgical never-events. For example, wrong body part cohort 606 is a cohort of surgical procedure never-event cohort 604 having members who have received a surgical procedure on the wrong body part. Thus, patients who have had the wrong kidney removed, or had a surgical procedure performed on the wrong knee may be found in wrong body part cohort 606. In an alternate embodiment, wrong body part cohort 606 may include cohorts based upon the particular body part upon which a surgical procedure was performed.

Wrong surgical procedure cohort 608 is a cohort of surgical procedure never-event cohort 604 having members who have received the wrong surgical procedure. Thus, a patient who was admitted to a hospital for a heart bypass but received a heart transplant would be included in wrong surgical procedure cohort 608. In addition, wrong surgical procedure cohort 608 may also include one or more cohort based upon categories, such as the types of surgical procedures that were administered.

Figure 7:
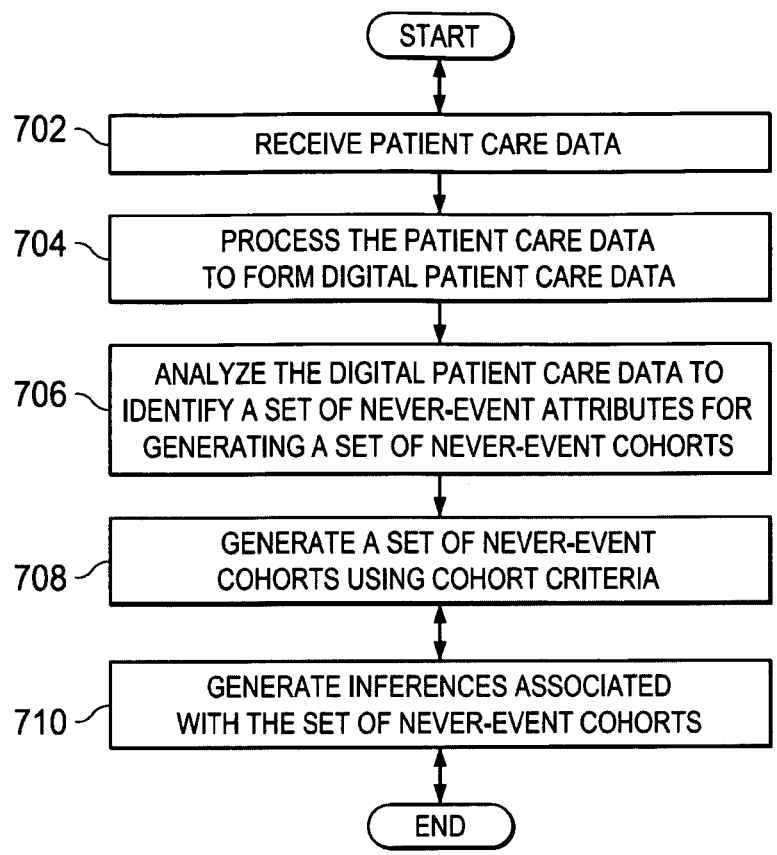
FIG. 7 is a flowchart of a process for generating never-event cohorts in accordance with an illustrative embodiment.

FIG. 7 is a flowchart of a process for generating never-event cohorts in accordance with an illustrative embodiment. The process depicted in FIG. 7 may be implemented by software components of a computing device. For example, steps 702-706 may be implemented in a patient care pattern processing engine, such as patient care pattern processing engine 316 in FIG. 3. Steps 708 may be implemented in a cohort generation engine, such as cohort generation engine 328 in FIG. 3. Step 710 may be implemented in an inference engine, such as inference engine 332 in FIG. 3.

The process begins by receiving patient care data (step 702). The patient care data is patient data, such as patient care data 311 in FIG. 3. The patient care data is processed to form digital patient care data (step 704). Thereafter, the digital patient care data is analyzed to identify a set of never-event attributes for generating never-event cohorts (step 706).

The process generates a set of never-event cohorts using cohort criteria (step 708). Inferences associated with the set of never-event cohorts may be generated (step 710) and the process terminates.

Figure 8:
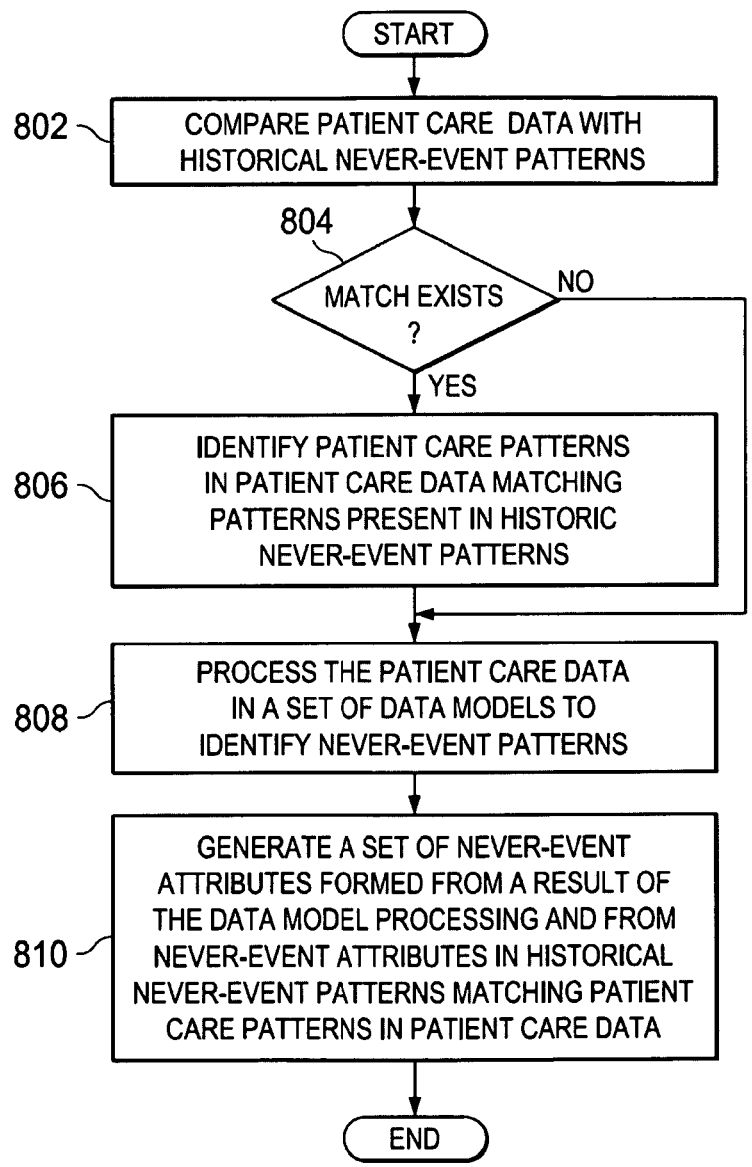
FIG. 8 is a flowchart of a process for processing patient care data in accordance with an illustrative embodiment.

FIG. 8 is a flowchart of a process for processing patient care data in accordance with an illustrative embodiment. The process depicted in FIG. 8 may be implemented in a software component, such as patient care pattern processing engine 316 in FIG. 3.

The process begins by comparing patient care data with historical never-event patterns (step 802). In one embodiment, the process compares patient care patterns in patient care data with historical patient care patterns. In another embodiment, the process compares metadata describing patient care patterns in patient care data with metadata associated with historical patient care patterns.

The process then makes a determination as to whether a match exists (step 804). If the process makes the determination that a match exists, the process identifies patient care patterns in patient care data that match patient care patterns present in historical never-event patterns (step 806). The patient care data is also processed in a set of data models (step 808), such as data models 320 in FIG. 3. The process then generates a set of never-event attributes formed from the results of the data model processing and from the never-event attributes of the historical patient care patterns which match patient care patterns in patient care data (step 810). The process terminates thereafter.

Returning to step 804, if the process makes the determination that no match exists between the patient care data and the historical patient care patterns, then the process continues to step 808.

Figure 9:
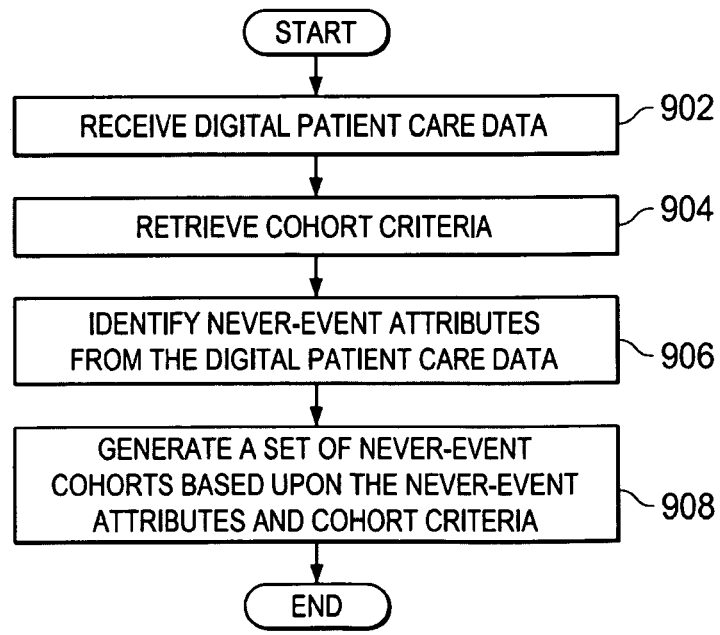
FIG. 9 is a flowchart of a process for generating never-event cohorts from digital patient care data in accordance with an illustrative embodiment.

FIG. 9 is a flowchart of a process for generating never-event cohorts based on processed patient care data in accordance with an illustrative embodiment. The process depicted in FIG. 9 may be implemented in a software component, such as cohort generation engine 328 in FIG. 3.

The process begins by receiving digital patient care data (step 902). The digital patient care data is digital patient care data, such as digital patient care data 312 in FIG. 3. The process then retrieves cohort criteria (step 904). Cohort criteria, such as cohort criteria 330 in FIG. 3, specify guidelines for creating a set of never-event cohorts.

The process identifies attributes from the digital patient care data (step 906). In one embodiment, the attributes in the digital patient care data are derived from the set of never-event patterns originally present in the patient care data. Thereafter, the process generates a set of never-event cohorts from the digital never-event data and the cohort criteria (step 908), and the process terminates.

Thus, the illustrative embodiments described herein provide a computer implemented method, apparatus, and computer program product for generating never-event cohorts. In one embodiment, in response to receiving patient care data derived from a population of patients, the patient care data is processed to form digital patient care data. The digital patient care data includes metadata describing a set of patient care patterns associated with one or more patients in the population of patients. The digital patient care data is analyzed using cohort criteria to identify a set of never-event attributes from the set of patient care patterns. The cohort criteria specify at least one never-event attribute from the set of never-event attributes for each cohort in a set of never-event cohorts. Thereafter, a set of never-event cohorts is generated. The set of never-event cohorts is formed from members selected from the population of patients, and each member of a cohort in the set of never-event cohorts has at least one never-event attribute in common.

The never-event cohorts generated by the method and apparatus disclosed above enable the grouping of members into cohorts having similar attributes. The never-event cohorts are formed from patient care data originating from medical records and event data captured at a patient care facility. Once formed, the never-event cohorts may then be included in a system-wide monitoring process to quickly and efficiently pass vital information to a real-time computational process. The generation of never-event cohorts, in the manner described above, obviates the need for manual selection of cohort attributes, thereby allowing the generation of more robust never-event cohorts. In addition, input from otherwise interested parties is unnecessary, thereby providing a more unbiased reporting of never-events. Once formed, the never-event cohorts may be used, for example and without limitation, for medical and diagnostic research, public health, demographic research, and safety and/or security applications.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories, which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for modifying a unit of medical equipment based on never-event cohorts, wherein a never-event is a preventable error experienced by a patient while receiving medical care, the computer implemented method comprising:

processing, by one or more processors and in response to receiving patient care data derived from a population of patients, the patient care data to form digital patient care data, wherein the digital patient care data comprises metadata describing a set of patient care patterns associated with one or more patients in the population of patients, and wherein the set of patient care patterns is one or more patterns of events that indicate a likely occurrence of a never-event at a patient care facility;

analyzing, by the one or more processors, the digital patient care data using cohort criteria to identify a set of never-event attributes from the set of patient care patterns, wherein the never-event attributes do not directly describe a never-event, wherein the cohort criteria specifies at least one never-event attribute from the set of never-event attributes for each cohort in a set of never-event cohorts, and wherein the never-event attributes identify common medical care procedures given to each cohort member;

receiving, by the one or more processors and from a set of sensors, facility event data, wherein the set of sensors comprises a motion sensor, a temperature sensor, a video camera, and a microphone capturing the facility event data, wherein the facility event data describes environmental conditions within a patient care facility, wherein the facility event data is a component of patient care data, wherein the patient care data comprises the set of patient care patterns, wherein the set of sensors further comprise an electrical fault sensor that detects an electrical fault in a unit of medical equipment used on patients in the patient care facility, and wherein the electrical fault causes an unwanted electrical shock to a user of the unit of medical equipment, wherein the unit of medical equipment is being used by a current patient;

forming, by the one or more processors, new digital patient care data from the patient care data;

generating, by the one or more processors, the set of never-event cohorts comprising members selected from the population of patients, wherein each member of a cohort in the set of never-event cohorts has the at least one never-event attribute in common, and wherein the unwanted electrical shock is the never-event at the patient care facility;

identifying, by one or more processors, a series of multiple events that led to the unwanted electrical shock suffered by the current patient;

in response to identifying the series of multiple events that led to the unwanted electrical shock suffered by the current patient, assigning, by one or more processors, the current patient to the set of never-event cohorts; and in response to a current patient being a member of the set of never-event cohorts, modifying, by a power controller in the unit of medical equipment being used by the current patient, the unit of medical equipment by turning off power to the unit of medical equipment in order to overcome a risk of the unwanted electrical shock to the current patient as caused by the electrical fault.

2. The computer implemented method of claim 1, wherein processing the patient care data further comprises:
identifying, by the one or more processors, a set of never-event patterns from the set of patient care patterns, wherein the set of never-event attributes are selected from the set of never-event patterns.

3. The computer implemented method of claim 2, wherein generating the set of never-event cohorts further comprises:
identifying, by the one or more processors, one or more cohorts from the set of never-event cohorts, wherein each of the one or more cohorts is based on a unique never-event attribute selected from the set of never-event patterns.

4. The computer implemented method of claim 1 further comprising:
identifying, by the one or more processors, each member of the set of never-event cohorts by patient care attributes for said each member.

5. The computer implemented method of claim 1, wherein analyzing the digital patient care data comprises the one or more processors analyzing the patient care data using historical never-event patterns and analyzing the patient care data with a set of data models.

6. The computer implemented method of claim 1 further comprising:
updating, by the one or more processors, historical never-event patterns with patient care patterns from the set of patient care patterns associated with a never-event attribute in the set of never-event attributes.

7. The computer implemented method of claim 1, further comprising:
generating, by the one or more processors, inferences based on the set of never-event cohorts, wherein the inferences indicate a cause of an associated never-event pattern.

8. A computer program product for restoring power to a patient care facility based on never-event cohorts, wherein a never-event is a preventable error experienced by a patient while receiving medical care, and wherein the computer program product comprises:
a non-transitory computer recordable-type medium;
first program instructions for processing patient care data derived from a population of patients to form digital patient care data in response to receiving the patient care data, wherein the digital patient care data comprises metadata describing a set of patient care patterns associated with one or more patients in the population of patients, and wherein the set of patient care patterns is one or more patterns of events that indicate a likely occurrence of a never-event at a patient care facility;
second program instructions for analyzing the digital patient care data using cohort criteria to identify a set of never-event attributes from the set of patient care patterns, wherein the never-event attributes do not directly describe a never-event, wherein the cohort criteria specifies at least one never-event attribute from the set of never-event attributes for each cohort in a set of never-event cohorts, and wherein the never-event attributes describe common medical care procedures given to each cohort member;
third program instructions for receiving, from a set of sensors, facility event data, wherein the set of sensors comprises a motion sensor, a temperature sensor, a video camera, a power sensor, and a microphone capturing the facility event data, wherein the facility event data describes environmental conditions within a patient care facility, wherein the power sensor detects a lack of power in the patient care facility, wherein the facility event data is a component of patient care data, and wherein the patient care data comprises the set of patient care patterns;
fourth program instructions for forming new digital patient care data from the patient care data;
fifth program instructions for generating the set of never-event cohorts comprising members selected from the population of patients, wherein each member of a cohort in the set of never-event cohorts has the at least one never-event attribute in common, wherein a current patient is a current patient in the patient care facility, and wherein the current patient is a member of the set of never-event cohorts;
sixth program instructions for identifying a series of multiple events that led to the unwanted electrical shock suffered by the current patient;
seventh in response to identifying the series of multiple events that led to the unwanted electrical shock suffered by the current patient, assigning, by one or more processors, the current patient to the set of never-event cohorts; and
eighth program instructions for transmitting, based on the set of never-event cohorts and in response to the current patient being the member of the set of never-event cohorts, an instruction to a power controller to switch from a primary power source for the patient care facility to a secondary power supply for the patient care facility; and wherein
the first program instructions, the second program instructions, the third program instructions, the fourth program instructions, the fifth program instructions, the sixth program instructions, the seventh program instructions, and the eighth program instructions are stored on the non-transitory computer recordable-type medium.

9. The computer program product of claim 8, further comprising:
ninth program instructions for identifying a set of never-event patterns from the set of patient care patterns, wherein the set of never-event attributes are selected from the set of never-event patterns, and wherein the ninth program instructions are stored on the non-transitory computer recordable-type medium.

10. The computer program product of claim 8, further comprising:
ninth program for identifying, from the set of never-event cohorts, one or more cohorts, wherein each of the one or more cohorts is based on a unique never-event attribute selected from a set of never-event patterns, and wherein the ninth program instructions are stored on the non-transitory computer recordable-type medium.

11. The computer program product of claim 8, further comprising:
ninth program instructions for identifying each member of the set of never-event cohorts by patient care attributes for said each member, wherein the ninth program instructions are stored on the non-transitory computer recordable-type medium.

12. The computer program product of claim 8, further comprising:
ninth program instructions for at least one of analyzing the patient care data using historical never-event patterns and analyzing the patient care data with a set of data models, wherein the ninth program instructions are stored on the non-transitory computer recordable-type medium.

13. The computer program product of claim 8 further comprising:
ninth program instructions for updating historical never-event patterns with patient care patterns from the set of patient care patterns associated with a never-event attribute in the set of never-event attributes, and wherein the ninth program instructions are stored on the non-transitory computer recordable-type medium.

14. The computer program product of claim 8, further comprising:
ninth program instructions for generating inferences based on the set of never-event cohorts, wherein the inferences indicate a cause of an associated never-event pattern, wherein the ninth program instructions are stored on the non-transitory computer recordable-type medium.

15. An apparatus for restoring power to a patient care facility based on never-event cohorts, wherein a never-event is a preventable error experienced by a patient while receiving medical care, the apparatus comprising:
a bus system;
a memory connected to the bus system, wherein the memory includes computer usable program code; and
a processing unit connected to the bus system, wherein the processing unit executes the computer usable program code to:
process patient care data derived from a population of patients to form digital patient care data in response to receiving the patient care data, wherein the digital patient care data comprises metadata describing a set of patient care patterns associated with one or more patients in the population of patients, and wherein the set of patient care patterns is one or more patterns of events that indicate a likely occurrence of a never-event at a patient care facility;
analyze the digital patient care data using cohort criteria to identify a set of never-event attributes from the set of patient care patterns, wherein the never-event attributes do not directly describe a never-event, wherein the cohort criteria specify at least one never-event attribute from the set of never-event attributes for each cohort in a set of never-event cohorts, and wherein the never-event attributes describe common medical care procedures given to each cohort member;
receive, from a set of sensors, facility event data, wherein the set of sensors comprises a motion sensor, a temperature sensor, a video camera, a power sensor, and a microphone capturing the facility event data, wherein the facility event data describes environmental conditions within a patient care facility, wherein the power sensor detects a lack of power in the patient care facility, wherein the facility event data is a component of patient care data, and wherein the patient care data comprises the set of patient care patterns;
form new digital patient care data from the patient care data;
generate the set of never-event cohorts comprising members selected from the population of patients, wherein each member of a cohort in the set of never-event cohorts has the at least one never-event attribute in common, wherein a current patient is a current patient in the patient care facility, and wherein the current patient is a member of the set of never-event cohorts;
identify a series of multiple events that led to the unwanted electrical shock suffered by the current patient;
in response to identifying the series of multiple events that led to the unwanted electrical shock suffered by the current patient, assign the current patient to the set of never-event cohorts; and
transmit, based on the set of never-event cohorts and in response to the current patient being the member of the set of never-event cohorts, an instruction to a power controller to switch from a primary power source for the patient care facility to a secondary power supply for the patient care facility.

16. The apparatus of claim 15, wherein the processing unit further executes the computer usable program code to identify a set of never-event patterns from the patient care patterns, wherein the set of never-event attributes are selected from the set of never-event patterns.

17. The apparatus of claim 15, wherein the processing unit further executes the computer usable program code to identify, from the set of never-event cohorts, one or more cohorts, wherein each of the one or more cohorts is based on a unique never-event attribute selected from a set of never-event patterns.

18. The apparatus of claim 15, wherein the processing unit further executes the computer usable program code for analyzing the digital patient care data for at least one of analyzing the patient care data using historical never-event patterns and analyzing the patient care data with a set of data models.

* * * * *